United States Patent [19]

Moyne

[11] Patent Number: 4,981,998

[45] Date of Patent: Jan. 1, 1991

[54] PROCESS FOR THE PREPARATION AND PURIFICATION OF D-HYDROXYPHENOXYPROPIONIC ACID

[75] Inventor: Jose Moyne, Caluire, France

[73] Assignee: Rhone-Poulenc Chimie, Courbevoie Cedex, France

[21] Appl. No.: 382,312

[22] Filed: Jul. 20, 1989

[30] Foreign Application Priority Data

Jul. 20, 1988 [FR] France ................................ 88 09793

[51] Int. Cl.$^5$ ............................................. C07C 59/48
[52] U.S. Cl. ...................................... 562/471; 560/61
[58] Field of Search ........................... 562/471; 560/61

[56] References Cited

U.S. PATENT DOCUMENTS 4,532,346  7/1985  Rehn .................................... 562/471

FOREIGN PATENT DOCUMENTS 192849  3/1986  European Pat. Off. .

Primary Examiner—Paul J. Killos
Attorney, Agent, or Firm—Finnegan, Henderson, Farabow, Garrett, and Dunner

[57] ABSTRACT

A process for the preparation of D-hydroxyphenoxypropionic acid and its purification from its reaction mixture containing the acid, together with inorganic salts and various organic impurities, by crystallization of D-hydroxyphenoxypropionic acid by cooling followed by washing the crystals of D-hydroxyphenoxypropionic acid by elution.

8 Claims, No Drawings

PROCESS FOR THE PREPARATION AND PURIFICATION OF D-HYDROXYPHENOXYPROPIONIC ACID

The present invention relates to a process for the preparation and purification of optically pure D-hydroxyphenoxypropionic acid. It relates more particularly to a process for its purification.

Aliphatic esters of optically pure D-hydroxyphenoxypropionic acid are intermediate to selective herbicides which are greatly sought after at the present time.

These esters may be obtained directly by a Walden inversion from an alkyl L-chloro- or bromopropionate and hydroquinone in the presence of a strong base in an aqueous or alcoholic medium. Unfortunately, the esters are easily hydrolyzed in these media and the chloropropionic moiety undergoes a racemization, as described by W. A. Cowdrey, E. D. Hargher and C. K. Ingold in the Journal of Chemical Society, 1208, (1937).

When, for example, according to Federal German Republic Patent No. DE 3,150,233, the above described water or alcohol medium is replaced with a polar aprotic medium such as dimethyl sulfoxide or dimethylformamide, a large quantity of disubstituted hydroquinone derivatives is obtained, which is difficult to separate off This disubstituted derivative initially consumes two moles of methyl L-chloropropionate, a most costly compound, which cannot be recovered.

European Patent No. 192,849 also a describes of a process for the preparation of 2-(4 hydroxyphenoxy) propionic acid by reaction of a chloro- or bromopropionic acid with hydroquinone in an extremely concentrated aqueous medium. In fact, the water/hydroquinone weight ratio is advantageously from 2 to 2.5. The ability to work in an extremely concentrated medium makes it possible:

- to limit the double substitution of hydroquinone,
- to increase the production efficiency, because a large quantity of the hydroquinone introduced can be converted, and
- to avoid the racemization of D-chloropropionic acid or of its sodium salt.

The ability to work in a concentrated medium, at the limit of viscosity which nevertheless permits adequate stirring, that is to say with a water/hydroquinone ratio of approximately 2.5, makes it possible therefore to obtain better selectivity for optically active D-hydroxyphenoxypropionic acid or its double sodium salt. Optically active D-hydroxyphenoxypropionic acid and its sodium salt contain a large quantity of hydroquinone which is removed after acidifying, as described in European Patent No. 192,849, by extraction with methyl isobutyl ketone.

The aqueous phase containing the hydroxyphenoxypropionic acid and its salt, resulting from this extraction operation, contains approximately 5% by weight of undesirable organic compounds to 15% of D-hydroxyphenoxypropionic acid.

The problem which European Patent No. 192,849 does not solve is the extraction of pure D-hydroxyphenoxypropionic acid from this mixture. D-hydroxyphenoxypropionic acid does not exhibit solubility or crystallization characteristics which are markedly different from those of the disubstituted derivative, or from those of the derivatives which are alkylated directly on the carbon of the aromatic nucleus of hydroquinone. Extraction of the pure product has consequently presented industry with a problem which is difficult to solve.

The present invention has made it possible to attain this objective, the preparation of D-hydroxyphenoxypropionic acid and its esters in pure form.

The preparation process comprises:

A first stage, in which alkyl L-chloro- or bromopropionate is hydrolyzed in water in the presence of a strong base, and the alcohol formed is removed by distillation;

A second stage, in which an aqueous alkaline suspension of hydroquinone is prepared;

A third stage, in which the aqueous alkaline suspension of hydroquinone is added to the solution of L-chloro- or bromopropionic acid in the form of its sodium salt so that the total quantity of water in the mixture is included in a weight proportion, calculated relative to hydroquinone, of from 2.4% to 2.8%;

A fourth stage, in which the mixture is acidified to a pH of from 4 to 6 and the hydroquinone is extracted with a ketone solvent that may be recycled to the second stage; and A fifth stage, in which the residual aqueous mixture is acidified to a pH of about 1 to precipitate the hydroxyphenoxypropionic acid, the remaining mixture separating into an aqueous phase and an oily phase.

One preferred preparation process comprises starting from methyl L-chloropropionate to prepare sodium L-chloropropionate by hydrolysis with an alkaline base according to the reaction:

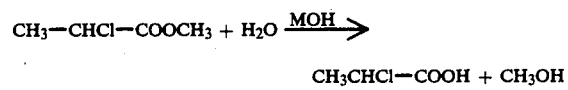

$$CH_3CHCl-COOH + CH_3OH$$

in which M is an alkali metal selected from sodium or potassium.

The alcohol and a proportion of the water are removed by distillation.

L-chloropropionic acid, in the form of its alkali metal salt obtained above, is brought into contact with the double sodium salt of hydroquinone to form the double salt of D-hydroxyphenoxypropionic acid.

The equation can be outlined in the following manner:

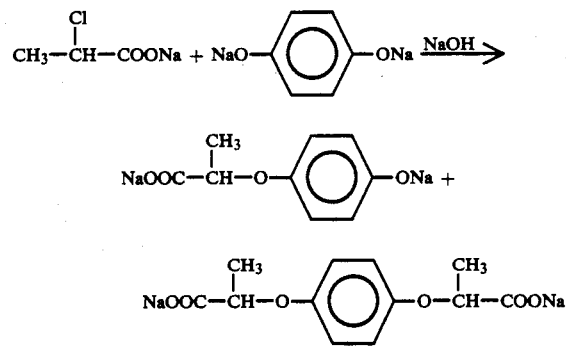

The double sodium salt of hydroquinone is formed by adding hydroquinone to sodium hydroxide, preferably in a weight ratio of between 1 and 1.5 times the weight of the sodium hydroxide.

The aqueous solution of L-chloropropionic acid in the form of its sodium salt is then added to the sodium suspension of hydroquinone so that the weight proportion of the total water of the mixture to the hydroquinone is from 2.4% to 2.8%. Below this proportion the medium cannot be stirred because it is too viscous; above this proportion the condensation produces a large quantity of disubstituted derivatives.

The reaction temperature is preferably from 30° to 50° C.

The molar quantity of hydroquinone which is introduced, relative to the L-chloropropionate, is preferably from 1.2 to 1.5. The reaction is therefore carried out with a molar excess of hydroquinone.

At the end of the reaction the mixture is acidified to a pH of approximately 6 to liberate the hydroquinone from its salt. The mixture becomes homogeneous.

Hydroquinone is extracted from the reaction mixture with an acetone-related solvent, preferably methyl isobutyl ketone.

The residual aqueous mixture is distilled so as to remove the ketone in solution in the aqueous phase, and is then acidified to a pH of less than 1 to precipitate the crude hydroxyphenoxypropionic acid.

The aqueous suspension containing the said precipitate has approximately the following composition, calculated relative to the hydroxyphenoxypropionic acid (HPPA)

|  |  |
|---|---|
| Hydroquinone = | 0.7 to 1% |
| Dialkoxyhydroquinone = | 10 to 15% |
| Nucleus-alkylated hydroquinone compounds = | 2 to 4% |
| Aliphatic acids = | 7 to 10% |
| NaCl = | 200% |
| HCl = | 7 to 10% |

The subject of the present invention also relates to a process for the purification of D-hydroxyphenoxypropionic acid from its preparative reaction mixture.

This process for the purification of optically pure D-hydroxyphenoxypropionic acid from its preparative reaction mixture, containing as impurities organic salts, hydroquinone, alkylated or alkoxylated derivatives of hydroquinone and racemic hydroxyphenoxypropionic acid, comprises acidifying the reaction mixture to a pH of approximately 1 to precipitate the hydroxyphenoxypropionic acid and the hydroquinone derivatives, the remaining reaction mixture separating into an aqueous phase and an oily phase, removing a part of the aqueous phase containing the inorganic salts, adding water and dissolving the hydroxyphenoxypropionic acid and the hydroquinone derivatives by heating, slowly cooling the solution to precipitate the crystals of optically pure D-hydroxyphenoxypropionic acid which are coated with at least a portion of the oily phase containing the remaining impurities, and washing the crystals by elution with water.

Broadly, a part of the aqueous phase remaining after precipitation of the hydroxyphenoxypropionic acid is removed by decanting and the precipitate is washed with a small quantity of water. Then the precipitate is heated in water to dissolve it and the mixture is cooled slowly to approximately ambient temperature. Following this, the D-hydroxyphenoxypropionic acid, which is coated with at least a portion of the oily phase, is separated by filtration and is washed by elution with water.

One preferred purification process comprises, in a first stage, removing by decanting a part of the aqueous phase containing the inorganic salts and washing the hydroxyphenoxypropionic acid precipitate 2 to 3 times with the minimum possible quantity of water. The quantity of washing water is preferably equal to 2 to 3 times the weight of hydroxyphenoxypropionic acid; these washings make it possible to dilute the content of inorganic salts by approximately 50%.

In a second stage, a quantity of water is added so that the total quantity of water is from 2 to 4 times the weight of hydroxyphenoxypropionic acid; the mixture is heated to a temperature of from 90° to 100° C. to dissolve all the components, and is cooled slowly to ambient temperature. The mixture separates into three phases:

a solid phase containing D-hydroxyphenoxypropionic acid, an oily phase containing hydroquinone, racemic hydroxyphenoxypropionic acid and the dialkoxylated derivative of hydroquinone, and an aqueous phase.

In a third stage, the D-hydroxyphenoxypropionic acid crystals, which are surrounded by and coated with an oily layer containing the various impurities, are filtered off. This oil is then displayed, in a fourth stage, by elution with water. This washing is carried out by elution to "push" the oil through the filter while producing as little turbulence as possible within the filter cake. The oil is thus displaced in a filter of the "piston" type with a minimum quantity of water so as to not dissolve the acid; this quantity is advantageously from 0.6 to 0.8 times the weight of the wet cake.

Using this purification technique, it is possible to obtain D-hydroxyphenoxypropionic acid with an efficiency of purification and recovery from the reaction synthesis mixture which is better than 90%, with the hydroxyphenoxypropionic acid having an optical purity better than 98% of the dextrorotatory derivative. The D-hydroxyphenoxypropionic acid is then esterified by any method known to a person skilled in the art.

Therefore, the combined process for the preparation and purification of optically pure D-hydrqxyphenoxypropionic acid is conducted in 9 stages, to wit:

In a first stage the alkyl L-chloro- or bromo-propionate is hydrolyzed in water in the presence of a strong base and the alcohol formed is removed by distillation;

In a second stage an aqueous alkaline suspension of hydroquinone is prepared;

In a third stage, the aqueous alkaline suspension of hydroquinone is added to the solution of L-chloro or bromopropionic acid in the form of its sodium salt, so that the total quantity of water in the mixture is included in a weight proportion, calculated relative to hydroquinone, of from 2.4% to 2.8%;

In a fourth stage, the mixture is acidified to a pH from 4 to 6 and the hydroquinone is extracted with a ketone solvent;

In a fifth stage, the residual aqueous mixture is acidified to a pH of about 1 to precipitate the hydroxyphenoxypropionic acid, and the remaining mixture separates into an aqueous phase and an oily phase;

In a sixth stage, a part of the aqueous phase is removed by decanting and the precipitate is washed with a small quantity of water;

In a seventh stage, the precipitate is dissolved by heating it in water, and the mixture is cooled slowly to about ambient temperature;

In an eighth stage, the D-hydroxyphenoxypropionic acid, coated with at least a portion of the oily phase, is separated off by filtration; and In a ninth stage, the D-hydroxyphenoxypropionic acid is washed by elution with water.

The present invention will be described more completely with the aid of the following example, which must not be considered as limiting the invention.

EXAMPLE 12.250 kg of methyl L-chloropropionate (100 moles) were introduced into the foot of a 50-liter reactor equipped with a distillation column and 19.080 kg of 21.4% strength sodium hydroxide were added over a one hour period at a temperature of 30° to 35° C.; the mixture was kept at this temperature for half an hour to complete the hydrolysis of the ester, and 6.350 kg of a mixture containing 50% of water and methanol were then distilled off.

This concentrated solution of sodium L-chloropropionate was used within 24 hours.

10.6 kg of sodium hydroxide (265 moles) in the form of 36% to 26% strength aqueous sodium hydroxide were introduced into a 100-liter enameled steel reactor.

13.7540 kg (125 moles) of hydroquinone were added over a one hour period and the temperature was maintained at 40° C. by cooling.

If the concentration is too high the hydroquinonate formed is unstirrable, and if the dilution is too great the content of disubstituted compound is increased.

The aqueous solution of sodium L-chloropropionate prepared above was added to this suspension of sodium hydroquinonate in water over 4-5 hours at 40° C. The mixture was kept at 40° C. for one to three hours until the content of hydroxyphenoxypropionic acid no longer increased (the reaction being followed by liquid phase chromatography).

The pH was adjusted to a value of 6 by adding concentrated hydrochloric acid and the excess hydroquinone was extracted with three quantities of methyl isobutyl ketone, that is, 36.9 kg of methyl isobutyl ketone in all.

The aqueous phase was distilled to remove the soluble methyl isobutyl ketone and was then acidified to pH<1 to precipitate the crude D-hydroxyphenoxypropionic acid.

The weight of the reaction mixture, 86 kg, contained:

| | |
|---|---|
| Hydroquinone | 0.100 kg |
| Hydroxyphenoxypropionic acid | 13.286 kg (73 moles, including 3 or 4 of racemic acid) |
| Dialkoxylated derivatives | 1.524 kg (6 moles) |
| C-alkylated derivatives | 0.254 kg |
| NaCl | 21.469 kg |
| HCl | 0.934 kg |
| Aliphatic acids | 1.140 kg |
| H$_2$O | 47.301 kg |
| TOTAL | 86.008 kg |

The precipitate of crude hydroxyphenoxypropionic acid was allowed to settle, 26.877 kg of the aqueous phase saturated with NaCl were drained off; 8.2 kg of water were added and the mixture was stirred and allowed to settle. 13.750 kg of aqueous phase were drained off again and 21.844 kg of water were added again to the reactor.

The mixture then had the following composition:

| | |
|---|---|
| Hydroquinone | 0.070 kg |
| Hydroxyphenoxypropionic acid | 12.847 kg — (70.6 moles) (D isomer + racemic acid) |
| Dialkoxylated derivatives | 1.27 kg — (5 moles) |
| C-alkylated derivatives | 0.250 kg |
| NaCl | 10.080 kg |
| HCl | 0.439 kg |
| H$_2$O | 49.919 kg |
| Aliphatic acids | 0.550 kg |
| TOTAL | 75.425 kg |

The mixture was heated to 95° C. to completely dissolve the various components and the temperature was then reduced very slowly from 90° to 70° C. The mixture became cloudy and milky, showing the appearance of an oil and not of crystals. Starting at 70° C. and down to 20° C., attractive crystals of dextrorotatory hydroxyphenoxypropionic acid appear.

Part of the oil was removed in the mother liquors by filtering under pressure, but the essential part was physically removed from the precipitate by being displaced with the smallest possible quantity of water, that is, approximately 9 kg of water.

If the washing liquors are not stirred so as not to dissolve the oil completely or partially in the water, they can be analyzed by high-pressure liquid chromatography and it was ascertained that there was an almost constant ratio between the various constituents:

| | in moles |
|---|---|
| Hydroquinon | 1% |
| Hydroxyphenoxypropionic acid | 54% (partly racemic) |
| C-alkylated derivatives | 8% (there were 3 different compounds) |
| Dialkoxylated derivatives | 37% (essentially the D-D stereoisomer) |
| Weight of the cake dried under vacuum at 80° C. | 11.766 kg (64.6 moles) |
| Purity of hydroxyphenoxypropionic acid | 99% |
| Content of Dialkoxylated derivatives | ≦1% |
| Enantiomeric excess: (chiral column chromatography) | 98 to 99% |

Out of 70 moles of hydroxyphenoxypropionic acid present at the end of the synthesis, 64.6 were recovered in the final product. This means a recovery yield of 92%.

The treatment has therefore enabled the removal of 5.5 moles of dialkoxylated derivatives, 3 to 4 moles of racemic hydroxyphenoxypropionic acid and the equivalent of one mole of the 3-C-alkylation products.

From this pure D-hydroxyphenoxypropionic acid it is possible to directly obtain chemically and optically pure esters without any separation problem.

What is claimed is:

1. A process for the purification of optically pure D-hydroxyphenoxypropionic acid from its preparative reaction mixture containing as impurities inorganic salts, hydroquinone and alkylated or alkoxylated derivatives of hydroquinone and racemic hydroxyphenoxypropionic acid, said process comprising acidifying said reaction mixture to a pH of about 1 to precipitate the hydroxyphenoxypropionic acid and the hydroquinone derivatives, the remaining reaction mixture separating into an aqueous phase and an oily phase, removing a part of the aqueous phase containing the inorganic salts, adding water and dissolving the hydroxyphenoxypropionic acid and the hydroquinone derivatives by heating, slowly cooling the solution to precipitate the crystals of optically pure D-hydroxyphenoxypropionic acid which are coated with at least a portion of said oily phase containing the remaining impurities, and washing the said crystals by elution with water.

2. The process as claimed in claim 1, wherein the heating to dissolve said hydroxyphenoxypropionic acid and hydroquinone derivatives is carried out at a temperature of 90° to 100° C.

3. The process as claimed in claim 1, wherein the quantity of water added to dissolve the hydroxyphenoxypropionic acid is from 2 to 4 times the weight of said acid.

4. The process as claimed in claim 1, wherein the quantity of water in elution of the crystals of D-hydroxyphenoxypropionic acid is from 0.6 to 0.8 times the weight of said crystals.

5. A process for the preparation and purification of optically pure D-hydroxyphenoxypropionic acid from hydroquinone and alkyl L-chloro- or bromopropionate which comprises:

in a first stage, hydrolyzing the alkyl L-chloro- or bromopropionate in water in the presence of a strong base and removing the alcohol formed by distillation, in a second stage, preparing an aqueous alkaline suspension of hydroquinone, in a third stage, adding the aqueous alkaline suspension of hydroquinone to the solution of L-chloro- or bromopropionic acid in the form of its sodium salt, so that the total quantity of water in the mixture is included in a weight proportion, calculated relative to hydroquinone, of from 2.4% to 2.8%, in a fourth stage, acidifying the mixture to a pH of from 4 to 6 and extracting the hydroquinone with a ketone solvent, in a fifth stage, acidifying the residual aqueous mixture to a pH of approximately 1 to precipitate the hydroxyphenoxypropionic acid, the remaining mixture separating into an aqueous phase and an oily phase, in a sixth stage, removing a part of the aqueous phase by decanting and washing the precipitate with a small quantity of water, in a seventh stage, heating the precipitate in water to dissolve it and cooling the mixture slowly to about ambient temperature, in an eighth stage, separating the D-hydroxyphenoxypropionic acid coated with at least a portion of said oily phase, by filtration, and in a ninth stage washing the D-hydroxyphenoxypropionic acid by elution with water.

6. The process as claimed in claim 5, wherein the quantity of water present in the seventh stage to dissolve the precipitate is from 2 to 4 times the weight of the precipitate.

7. The process as claimed in claim 5, wherein the quantity of water used in the elution of the D-hydroxyphenoxypropionic acid is from 0.6 to 0.8 times the weight of the acid.

8. The process as claimed in claim 5, wherein the hydroquinone extracted with a ketone solvent in the fourth stage is recycled to the second stage.

* * * * *